United States Patent
Kuhrs et al.

(10) Patent No.: US 7,253,280 B2
(45) Date of Patent: Aug. 7, 2007

(54) TWO-STAGE REACTOR FOR THE PRODUCTION OF MELAMINE

(75) Inventors: Christian Kuhrs, Heidelberg (DE); Eckehard Danz, Ludwigshafen (DE); Wolfgang Steiner, Friedelsheim (DE); Ralf-Thomas Rahn, Mannheim (DE); Thomas Grassler, Limburgerhof (DE); Reiner Geier, Mannheim (DE); Klaus Harth, Hong Kong (CN); Markus Hölzle, Kirchheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/542,306

(22) PCT Filed: Jan. 16, 2004

(86) PCT No.: PCT/EP2004/000327

§ 371 (c)(1),
(2), (4) Date: Nov. 18, 2005

(87) PCT Pub. No.: WO2004/065371

PCT Pub. Date: Aug. 5, 2004

(65) Prior Publication Data

US 2006/0167250 A1 Jul. 27, 2006

(30) Foreign Application Priority Data

Jan. 17, 2003 (DE) .................. 103 01 703
Aug. 14, 2003 (DE) .................. 103 37 501

(51) Int. Cl.
*C07D 251/60* (2006.01)
*C07D 251/62* (2006.01)

(52) U.S. Cl. .................... 544/201; 544/203
(58) Field of Classification Search ............... 544/201, 544/203

See application file for complete search history.

(56) References Cited

U.S. PATENT DOCUMENTS 3,300,493 A  1/1967  Hamprecht et al.
5,350,849 A  9/1994  van de Moesdijk et al.

FOREIGN PATENT DOCUMENTS

DE   1209570      3/1964
JP   08-027126 A  1/1996

OTHER PUBLICATIONS

Thianrangi Huagong, 2001, vol. 26, pp. 23-25.

*Primary Examiner*—Venkataraman Balasubramanian
(74) *Attorney, Agent, or Firm*—Connolly Bove Lodge & Hutz LLP

(57) ABSTRACT

The present invention relates to a process for the catalytic preparation of melamine by decomposition of urea over particular solid catalysts using a main reactor and an after-reactor. A catalyst having a low Lewis acidity is used in the main reactor and a catalyst having an equal or preferably higher Lewis acidity is used in the after-reactor.

19 Claims, 4 Drawing Sheets

TWO-STAGE REACTOR FOR THE PRODUCTION OF MELAMINE

This application is a National Stage of PCT/EP2004/000327 filed Jan. 16, 2004 which in turn claims priority from German Applications 103 01 703.8 filed Jan. 17, 2003 and 103 37 501.5, filed Aug. 14, 2003.

TECHNICAL FIELD

The present invention relates to a process for preparing melamine by catalytic decomposition of urea. The process of the present invention is a two-stage process in which catalysts of differing acidity are used in the two stages.

BACKGROUND OF THE INVENTION

Melamine, whose structure is represented by the formula I,

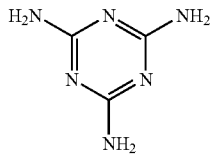

is used for preparing melamine resins by reaction with carbonyl-containing compounds. The resins are used, inter alia, as plastics and in paints and varnishes. The preparation of melamine by decomposition of urea is a known reaction which is utilized in a number of variants by the chemical industry. A distinction is made in principle between the high-pressure process and the low-pressure process. The high-pressure process is carried out at pressures of >about 80 bar (abs.) and temperatures of >370° C. in the absence of catalysts.

However, the low-pressure process which is carried out at pressures from about 1 to 10 bar (abs.) and temperatures of from 370 to 430° C. is of greater importance in the context of the present invention. It is known that the reaction proceeds in two steps. In the first, endothermic step, urea reacts to form ammonia and isocyanic acid which trimerizes in a second, exothermic step to form melamine and liberate $CO_2$. The following equations describe the individual reactions.

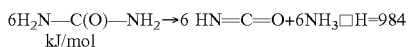

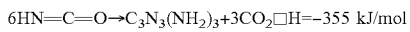

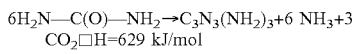

There are three main variants of the low-pressure process, which are described in greater detail below.

In the process of Linz-Chemie, the reaction is carried out in two stages. In the first stage, molten urea is decomposed in a fluidized bed of sand at 350° C. and 3.5 bar (abs.) to form ammonia and isocyanic acid. Isocyanic acid is subsequently converted catalytically into melamine at 450° C. and atmospheric pressure in a fixed-bed reactor. The catalyst is generally an aluminum oxide catalyst.

The DSM-Stamicarbon process is a single-stage process carried out at about 7 bar (abs.). Catalysts used are aluminum silicates which are employed as a fluidized bed. The fluidizing gas is pure ammonia which is recovered by work-up of the offgas.

Finally, there is the BASF process. Here too, the reaction is carried out in a fluidized bed using aluminum oxide or aluminum oxide/silicon dioxide catalysts at a low pressure (about 2 bar abs.). The gas used for the fluidized bed is recycled gas from the reactor which comprises $NH_3$ and $CO_2$ and has previously been freed of impurities, generally by treatment with a urea melt which takes up the impurities.

A problem which frequently occurs when carrying out all the abovementioned catalytic processes, which in principle offer the advantage of simpler, cheaper apparatuses compared to the noncatalytic processes, is the deposition of higher condensation products of melamine on the surface of the catalyst (coating). An example which may be mentioned here is melem ($C_6H_6N_{10}$, 2,5,8-triamino-1,3,4,6,7,9,9b-heptaazaphenalene) which is a three-ring compound made up of three fused triazine rings. The excessive deposition of condensation products is associated with deactivation of the catalyst, requiring regeneration of the catalyst, for example by thermal treatment and/or treatment with steam, air or ammonia, but in an extreme case also making replacement of the catalyst necessary. Since, in addition, deposition of condensation products on the catalyst proceeds relatively quickly to give a steady-state concentration of these products, deactivation frequently occurs after a very short period of time, so that periodic regeneration is not feasible because of the short time intervals.

There have hitherto been no systematic studies nor knowledge regarding the properties or compositions which a catalyst used in the synthesis of melamine has to have in order to achieve a high yield or a low degree of decomposition.

JP-A 08 027 126 claims a $\gamma$-$Al_2O_3$ catalyst having defined acidity limits for the synthesis of melamine.

Thianranqi Huagong, 2001, volume 26, pages 23 to 25 (cited on the basis of CA 136:135396) discloses that active catalysts for the synthesis of the melamine can be obtained by mixing $Al_2O_3$ with zeolites or zeolites containing metal cations. The activity obtained is ascribed to the acidic centers of the catalyst.

However, it has been found that the use of catalysts having an increased acidity is not able to solve the problems of catalyst deactivation, in particular as a result of deposit formation, and the low conversions associated therewith.

It is an object of the present invention to provide a process by means of which it is possible to obtain high conversions and melamine yields without premature deactivation of the catalyst as a result of deposit formation occurring, particularly under the chosen reaction conditions.

We have found that this object is achieved by a process for the catalytic preparation of melamine by decomposition of urea over solid catalysts using a main reactor and an after-reactor, wherein a catalyst having a low Lewis acidity is used in the main reactor and a catalyst having an equal or higher Lewis acidity is used in the after-reactor.

DESCRIPTION OF THE INVENTION

The present invention is based on the recognition that although the use of a catalyst having a high Lewis acidity gives a high conversion of the starting material urea to melamine and thus leads to high reaction yields, the formation of deposits on the catalyst used also occurs rapidly. The desired effect of the high conversion is thus rapidly outweighed by the deactivation of the catalyst as a result of deposit formation.

Since the measures which have been employed for avoiding or reversing formation of deposits are expensive and, in addition, deposit formation occurs quickly, it has been found that it is advantageous to carry out the formation of melamine in two separate reactors (main reactor and after-reactor). A catalyst of low Lewis acidity is used in the main reactor, resulting in a comparatively low conversion but also in low deposit formation occurring. A catalyst having the same Lewis acidity or a higher Lewis acidity is used in the after-reactor. The catalyst in the after-reactor preferably has a higher Lewis acidity, which makes a very high conversion possible. It is thus possible to achieve a high overall conversion but at the same time low deactivation of both the catalyst used in the main reactor and that used in the after-reactor.

In the main reactor, in which both the dissociation of urea to form isocyanic acid and the trimerization to form melamine occur but the latter reaction in particular occurs only incompletely, the catalyst can in principle by present in any form known to those skilled in the art, for example as a fixed bed, fluidized bed, circulating fluidized bed or moving bed. The catalyst is preferably used as a fluidized bed.

The catalyst used in the main reactor preferably comprises at least one mineral from the group consisting of aluminum oxides, silicon oxides and aluminosilicates and mixtures of various aluminum oxides, silicon oxides and/or aluminosilicates. It particularly preferably comprises at least one mineral from the group consisting of bayerite, boehmite, gibbsite, montmorillonite, bentonite and muscovite, in particular bentonite. The catalyst can also consist entirely of the minerals mentioned.

The abovementioned minerals may have been activated in a manner known to those skilled in the art before use in order to achieve a desired acidity, for example by thermal treatment. Since a thermal treatment generally increases the acidity of the minerals mentioned, it is generally not carried out in the case of the catalysts used in the main reactor.

The catalysts used in the main reactor preferably have a surface Lewis acidity of from 0.3 to 1.8 µmol/g, more preferably from 0.5 to 1.5 µmol, in particular from 0.8 to 1.2 µmol/g. The values indicated were obtained by means of acidity measurements in a high-vacuum Fourier transform infrared spectrometer (HV-FTIR) at 390° C. using pyridine as probe molecule and the Lewis centers characterized by different IR absorption bands were determined quantitatively by integration of the peak areas. The method described in Turk. J. Chem. 23 (1999), pages 319 to 327, was employed for this purpose. The values were determined at an internal diameter of the holder for the pressed catalyst pellet of 5.1 mm.

Typical fluidized-bed catalysts have BET surface areas of from 50 to 350 $m^2$/g, preferably from 100 to 250 $m^2$/g. Pore volumes are in the range from 0.1 to 1.0 ml/g. The average particle size of the catalysts is from 10 to 500 µm.

The process in the presence of the specified catalysts is carried out at from 350 to 450° C., preferably from 380 to 420° C., an absolute pressure of from 1 to 15 bar, preferably from 1 to 10 bar, in particular from 5 to 8 bar, a residence time over the fluidized bed of from 1 to 50 s, preferably from 2 to 30 s, and a space velocity over the catalyst of from 20 to 700 kg of urea/t (cat)·h, preferably from 50 to 500 kg of urea/t (cat)·h.

The main reactor usually has a cylindrical or conical shape. In one embodiment of the present invention, the fluidized-bed reactor employed as main reactor has a conical configuration. This achieves an increased velocity of the incoming gas and thus more stable fluidization behavior.

The catalyst used in the after-reactor preferably has a volume-standardized surface Lewis acidity under the reaction conditions which is from 1.5 to 6 times, preferably from 3 to 5 times, that of the catalyst used in the main reactor.

The surface acidity of the catalysts used in the after-reactor is preferably from 2 to 12 µmol/g, more preferably from 3 to 10 µmol/g, in particular from 3.5 to 6 µmol/g. The values given were obtained by acidity measurements in a high-vacuum Fourier transform infrared spectrometer (HV-FTIR) at 390° C. using pyridine as probe molecule and the Lewis centers characterized by different IR absorption bands were determined quantitatively by integration of the peak areas. The method described in Turk. J. Chem. 23 (1999), pages 319 to 327, was employed for this purpose. The values were determined at an internal diameter of the holder for the pressed catalyst pellet of 5.1 mm.

Like the catalysts used in the main reactor, the catalyst in the after-reactor preferably comprises at least one mineral from the group consisting of aluminum oxides, silicon oxides and aluminosilicates and mixtures of aluminum oxides, silicon oxides and/or aluminosilicates. The catalysts used in the after-reactor comprise from 0 to 60% by weight, preferably from 5 to 50% by weight, of $SiO_2$ and from 100 to 40% by weight, preferably from 95 to 50% by weight, of $Al_2O_3$. Preference is given to using aluminosilicate catalysts. The catalysts have BET surface areas of from 150 to 400 $m^2$/g, preferably from 200 to 350 $m^2$/g.

The measures required to achieve the necessary acidity are known to those skilled in the art. The desired acidity can be achieved by incorporation of ions of differing valence into a given mineral (for example silicon dioxide in aluminum oxide) and/or heat treatment. In a preferred embodiment of the present invention, the minerals mentioned are activated by thermal treatment at from 350 to 950° C., preferably from 450 to 750° C., before use.

The pore volumes of the catalysts are from 0.1 to 1.5 ml/g, preferably from 0.2 to 0.9 ml/g ($N_2$), or from 0.1 to 2.0 ml/g, preferably from 0.2 to 1.0 ml/g (Hg porosimetry). The pore diameters are from 10 to 100 Å, preferably from 30 to 90 Å.

The process of the present invention is carried out at residence times in the after-reactor of from 0.1 to 20 s, preferably from 0.5 to 10 s, and space velocities over the catalyst in the after-reactor of from 0.05 to 2 g of HNCO/g (cat)·h, preferably from 0.1 to 1 g of HNCO/g (cat)·h. The temperature is from 350 to 500° C., preferably from 390 to 450° C., and the pressure is from 1 to 15 bar absolute, preferably from 1 to 10 bar, in particular from 5 to 8 bar absolute.

In the after-reactor, the catalyst can be present in a suitable form known to those skilled in the art, for example as a fixed bed or fluidized bed. It has been found to be advantageous for the catalyst in the after-reactor to be in a form which allows only a small degree of backmixing to occur during the reaction. This is the case, for example, for fixed-bed catalysts, so that the use of a fixed-bed catalyst in the after-reactor is preferred. The fixed-bed catalyst is advantageously present as shaped bodies. Preference is given to choosing shaped bodies through which the fine catalyst dust carried from the main reactor can pass, for example hollow extrudates, monoliths, star extrudates, pellets or crushed material. Particularly useful shapes are honeycombs and hollow extrudates, in particular honeycombs. Among the shaped bodies mentioned, honeycombs have the best properties in respect of the pressure differences during passage of the reaction gases.

Preference is given to using honeycombs which consist entirely of γ-aluminum oxide or consist essentially of γ-aluminum oxide. Honeycombs comprising from 60 to 100% by weight of γ-$Al_2O_3$ and from 0 to 40% by weight of $SiO_2$ are preferred.

The composition to be shaped into honeycombs is mixed dry and admixed with a peptizing agent, preferably nitric acid, and water and is then compounded in a pan mill. Suitable peptizing agents are known to those skilled in the art. It is also possible, if desired, to use organic auxiliaries which decompose without leaving a residue on heating. Examples are carbonates and cellulose derivatives. Specific examples include ammonium carbonate, ammonium oxalate and hydroxymethylcellulose (for instance the product marketed under the name Walocel®, Wolff Walsrode). The compounded composition is then extruded under pressure to give the desired honeycomb geometry. The shaped bodies are dried and finally calcined, preferably at <600° C.

The process is preferably carried out so that the major part of the conversion occurs in the main reactor and a smaller proportion of the conversion (residual conversion) occurs in the after-reactor.

The invention is illustrated by the following examples. In references to the drawings, A=conversion [%]; B=organic deposit [% by weight]; C=running time [h].

EXAMPLES

Example 1 (Comparative Example)

In a pilot reactor having a diameter of 80 cm and a catalyst bed height of about 8 m, urea was converted into melamine at about 400° C. The three catalysts examined (calcined silicon-doped aluminum oxide (cat 1), calcined aluminum oxide (cat 2) and uncalcined aluminosilicate of the montmorillonite type (cat 3)) had Lewis acidities under reaction conditions of 4.4, 3.6 and 1.0 μmol/g, respectively. The fluidizing gas flow was about 300 standard m³/h.

Figure 1:
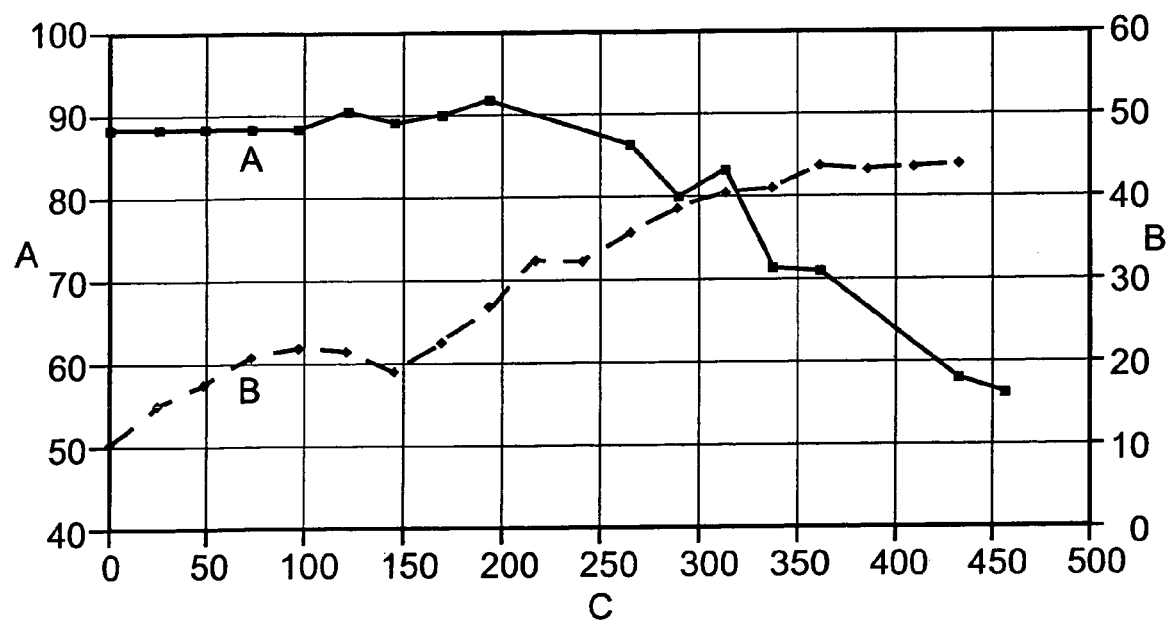
FIG. 1 compares the catalyst deactivation of calcined silicon-doped aluminumoxide (A) with the buildup of organic deposit (B) over time (C).

As can be seen from FIG. 1, the initial conversion of the most acidic catalyst (cat 1) is the highest at about 90%. However, catalyst deactivation takes place after a running time of only about 250 hours, and after 450 hours the conversion has dropped to below 60%. The catalyst deactivation is accompanied by the buildup of an organic deposit on the catalyst, which is responsible for the deactivation.

Figure 2:
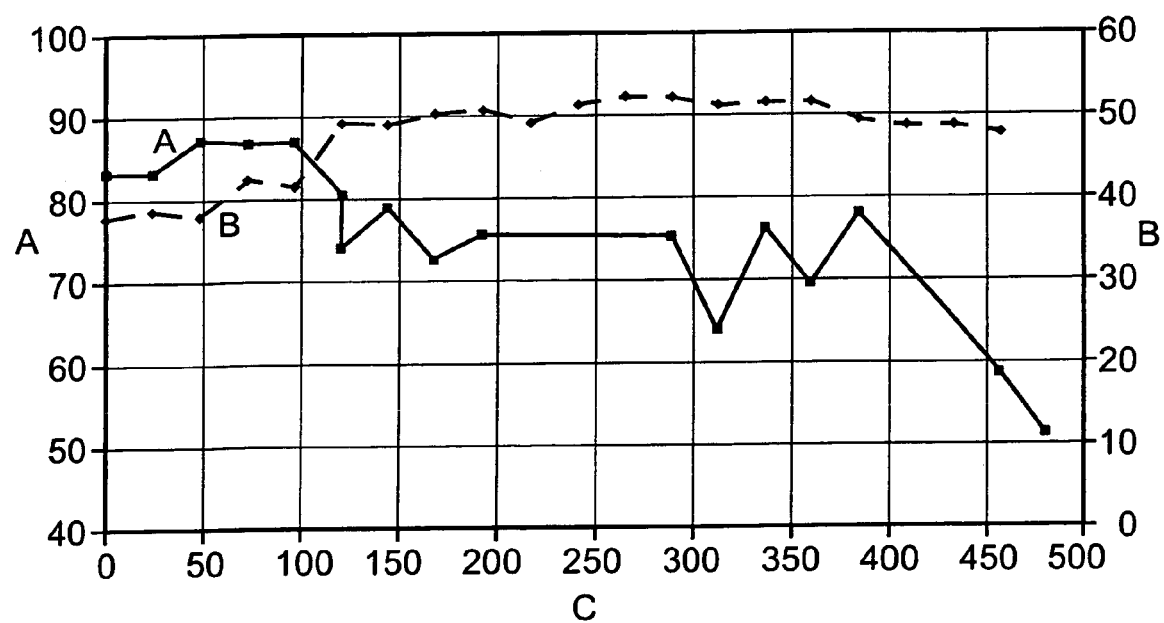
FIG. 2 compares the catalyst deactivation of calcined aluminum oxide (A) with the buildup of organic deposit (B) over time (C).

The somewhat less acidic catalyst having a Lewis acidity of 3.6 μmol/g (cat 2) displays a somewhat lower initial conversion of about 85%, which also decreases in parallel with the formation of an organic deposit (FIG. 2).

Figure 3:
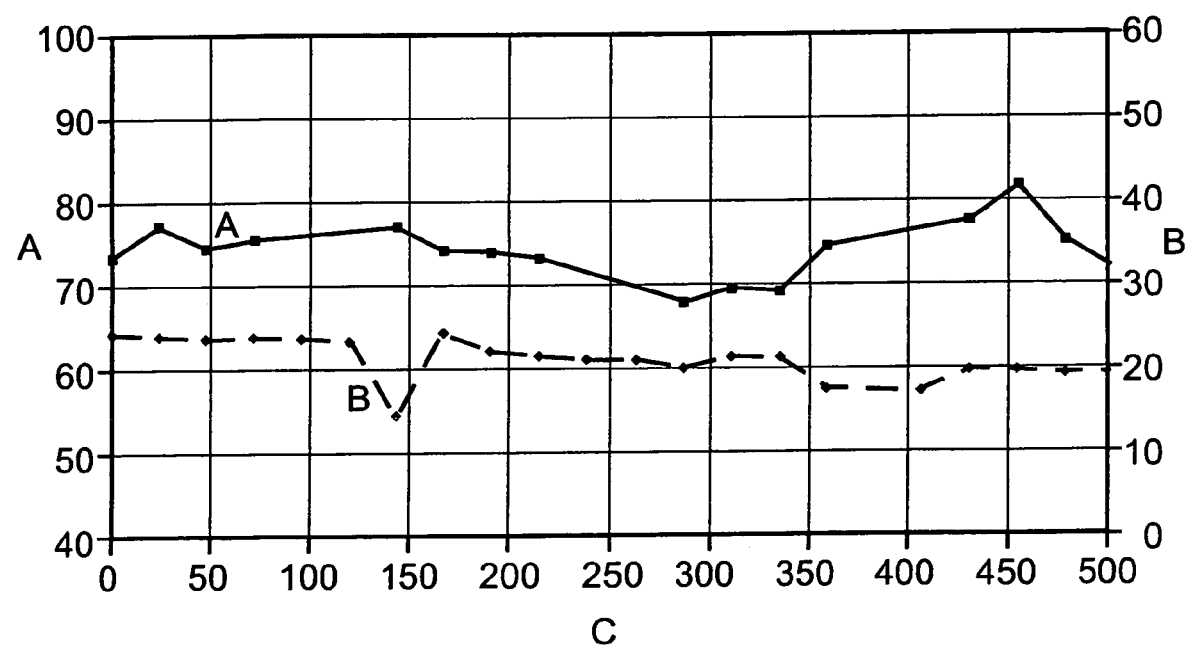
FIG. 3 compares the catalyst deactivation of uncalcined aluminosilicate of the montmorillonite type (A) with the buildup of organic deposit (B) over time (C).

FIG. 3 shows the corresponding test using the least acidic catalyst (cat 3, Lewis acidity only 1 μmol/g). The catalyst displays a conversion of only about 75%, but operates at a constant conversion because of the constant organic deposit.

It is thus found that although acidic catalysts ensure a high conversion, they are quickly deactivated. Catalysts having a lower acidity are less active, but suffer only insignificant deactivation.

Example 2

30 standard m³/h of a gas from a fluidized-bed reactor operated using the least acidic catalyst (cat 3) from example 1 were fed into a fixed-bed after-reactor having a diameter of 13.5 cm and a catalyst bed height of 1.5 m.

The catalyst used in the fixed-bed after-reactor was 10×20×5 mm hollow extrudates of silicon-doped aluminum oxide which had the composition 95% of $Al_2O_3$ and 5% of $SiO_2$ and had been calcined overnight at 550° C. after extrusion.

Figure 4:
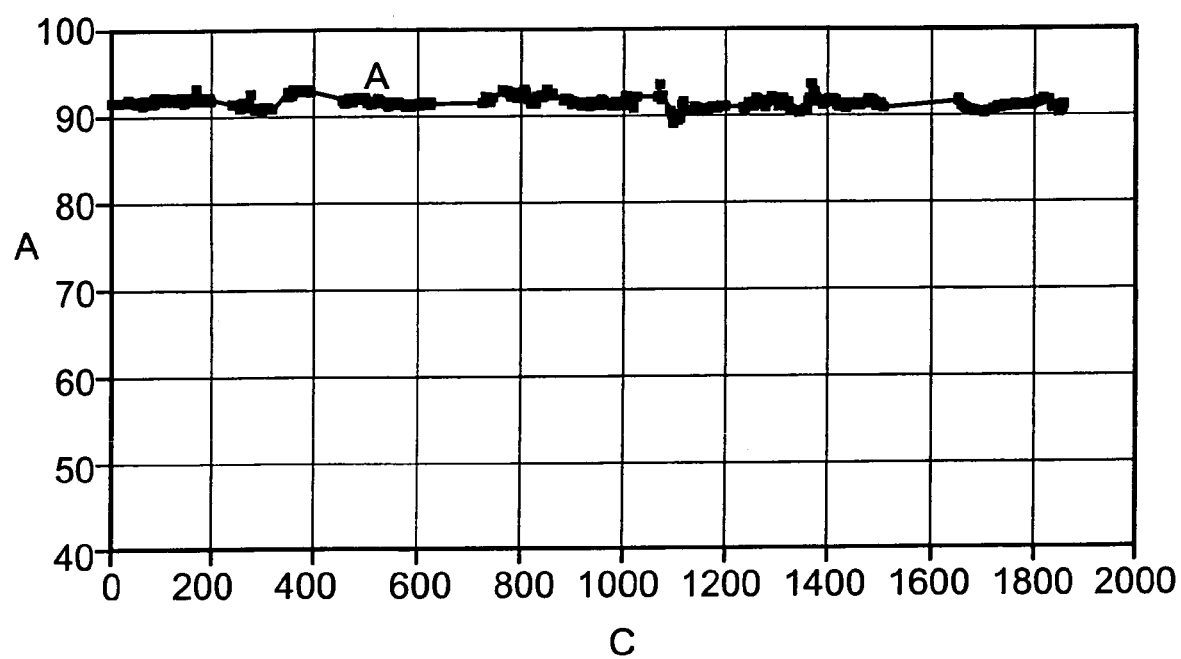
FIG. 4 compares the catalyst deactivation of uncalcined aluminosilicate of the monmorillonite type (A) with the buildup of organic deposit (B) at 400° C. at a pressure of 1.5 bar over time (C).

At about 400° C. and a pressure of 1.5 bar absolute, it was able to be demonstrated that a period of operation of >1500 hours at >90% total conversion without deactivation of the catalysts is possible (FIG. 4).

As a result of the combination of main reactor and after-reactor containing catalysts of differing acidity, a high conversion at high selectivity combined with low catalyst deactivation is observed.

The initial and final conversions achieved in example 1 and 2 are summarized once again in the following table.

TABLE 1

Conversions in examples 1 and 2

|  | $Conversion_{initial}$ (%) | $Conversion_{500\ h}$ (%) |
|---|---|---|
| Catalyst 1 | 88 | 56 |
| Catalyst 2 | 83 | 51 |
| Catalyst 3 | 73; constant | |
| Catalyst 3 plus after-reactor | 92; constant | |

Example 3

3 kg of a material consisting of 5% of $SiO_2$ and 95% of aluminum oxide hydroxide and 7 kg of a material consisting of 5% of $SiO_2$ and 95% of γ-$Al_2O_3$ are mixed dry for 5 minutes and, after addition of 0.635 kg of 69.3% strength $HNO_3$, diluted with 2.5 kg of deionized water and admixed with a further 4.3 kg of deionized water during compounding in a Mix-Muller.

Honeycombs having an edge length of 45×45 mm and length of 320 mm and possessing 6×6 cells having internal dimensions of 5.7×5.7 mm and a web thickness of 1.8 mm are extruded at a mold pressure of 50 bar and a temperature of 20° C. The shaped bodies are dried at room temperature. In a drying oven, the honeycombs are dried at 30° C. for 24 hours, then in 10° C. steps for 24 hours in each case up to 60° C. The honeycombs are dried at 60° C. for a further 24 hours. The honeycombs are finally calcined at 500° C. for 7 hours.

We claim:

1. A process for the catalytic preparation of melamine by decomposition of urea over solid catalysts using a main reactor and an after-reactor, wherein a catalyst having a low Lewis acidity is used in the main reactor and a catalyst having a higher Lewis acidity is used in the after-reactor such that said catalyst used in said after-reactor has a volume-standardized surface Lewis acidity of 1.5 to 6 times that of said catalyst used in said main reactor.

2. A process as claimed in claim 1, wherein the catalyst in the main reactor comprises at least one mineral from the group consisting of aluminum oxides, silicon oxides and aluminosilicates and mixtures thereof.

3. A process as claimed in claim 1, wherein the catalyst in the main reactor is present as a fluidized bed.

4. A process as claimed in claim 3, wherein the main reactor has a conical or cylindrical configuration.

5. A process as claimed in claim 1, wherein the acidity of the catalyst used in the main reactor is from 0.3 to 1.8 µmol/g.

6. A process as claimed in claim 1, wherein the acidity of the catalyst used in the after-reactor is from 2 to 12 µmol/g.

7. A process as claimed in claim 1, wherein the catalyst in the after-reactor comprises from 0 to 60% by weight of $SiO_2$ and from 100 to 40% by weight.

8. A process as claimed in claim 1, wherein the catalyst in the after-reactor comprises at least one mineral from the group consisting of aluminum oxides, silicon oxides and aluminosilicates and mixtures of aluminum oxides, silicon oxides and/or aluminosilicates.

9. A process as claimed in claim 1, wherein the catalyst in the after-reactor is activated at from 350 to 950° C. before use.

10. A process as claimed in claim 1, wherein the catalyst in the after-reactor has a BET surface area of from 150 to 400 m$^2$/g.

11. A process as claimed in claim 1, wherein the pore volumes of the catalysts are from 0.1 to 1.5 ml/g or from 0.1 to 2.0 ml/g, (Hg porosimetry), and the pore diameters are from 10 to 100 Å.

12. A process as claimed in claim 1, wherein the residence times in the after-reactor are from 0.1 to 20 s and the space velocities over the catalyst are from 0.05 to 2 g of HNCO/g (cat)·h.

13. A process as claimed in claim 1, wherein the residence times in the main reactor are from 1 to 50 s and the space velocities over the catalyst are from 20 to 700 kg of urea/t (eat)·h.

14. A process as claimed in claim 1, wherein the reaction in the main reactor is carried out at from 350 to 450° C. and a pressure of from 1 to 15 bar.

15. A process as claimed in claim 1, wherein the reaction in the after-reactor is carried out at from 350 to 500° C. and a pressure of from 1 to 15 bar.

16. A process as claimed in claim 1, wherein the catalyst in the after-reactor is present as a fixed bed.

17. A process as claimed in claim 1, wherein the catalyst in the main reactor is present as a fluidized bed and that in the after-reactor is present as a fixed bed.

18. A process as claimed in claim 16, wherein the catalyst is present as monolith, hollow extrudate, star extrudate, pellets or crushed material.

19. A process as claimed in claim 2, wherein the catalyst comprises at least one mineral from the group consisting of bayerite, boehmite, gibbsite, montmorillonite, bentonite and muscovite.

* * * * *